US00PP09940P

United States Patent [19]

Friday

[11] Patent Number: Plant 9,940

[45] Date of Patent: Jul. 1, 1997

[54] 'P.F. 25' PEACH TREE

[75] Inventor: Paul Jan Friday, Coloma, Mich.

[73] Assignee: Paul J. Friday, Coloma, Mich.

[21] Appl. No.: 574,400

[22] Filed: Dec. 18, 1995

[51] Int. Cl.[6] ..... A01H 5/00

[52] U.S. Cl. ..... Plt./43.2

[58] Field of Search ..... Plt./43.2

*Primary Examiner*—James R. Feyrer
*Attorney, Agent, or Firm*—Fred P. Kostka

[57] ABSTRACT

A new and distinct variety of peach, *Prunrus persica*, tree having the following unique combination of desirable features:

1. The new and distinct variety of peach tree is above average height and of upright growth and a regular and productive bearer of peaches.
2. Producing a very firm fruit having a resilient flesh texture.
3. Blossoms are non-showy when in full bloom.
4. A substantially oval spherical fruit with skin of light red color overlying a yellow which covers approximately thirty percent (30%) of its surface at maturity.
5. Late maturing fruit of good taste.
6. A late maturing fruit of good storage and shelf life.

1 Drawing Sheet

ORIGIN OF VARIETY

The new peach tree (hereinafter referred to as the P.F. 25 peach tree) was originated by Paul Friday in the experimental orchard, which is maintained for the purposes of breeding peach trees, at Paul Friday farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The send producing parent trees are maintained solely as proprietary trees for breeding purposes and have not been relesed from the experimentl orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, P.F. 25, was a selection from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrated that such reproduction of the characteristics of the tree are consistent and are established and transmitted through succeeding propagation.

SUMMARY OF THE VARIETY

The new and distinct variety of peach tree is above average height and of upright growth and a regular and productive bearer of peaches. A distinct characteristic of the P.F. 25 peach tree is its medium vigor having growth of about twenty-four inches (24") per year. The blossoms bloom in mid-season and are characterized by being contracted or partially spread to approximately ¾ inch when in full bloom. At the same time the five petals of the blossoms are of lesser length than the length of petals of the normal showy blossom as exemplified by the Loring peach blossom.

The blossoms of the present peach tree at full bloom may be characterized as being non-showy. More specifically, the blossoms of the present peach tree have radially projecting and angularly spaced five blossom petals to form a blossom having a diameter of about ¾ measured across the blossoms.

The flesh of the fruit of the present peach tree is firm and is yellow.

The skin is smooth having moderate to little down and is of light red color overlying a yellow ground color. The yellow background covers approximately thirty percent (30%) of its surface at maturity. At maturity, the peach is spherical having an average diameter of about 2⅝".

The fruit produced by this tree has firm, and non-melting flesh, and thereby has the attendant resistance to blemishes and soft spots in harvesting, shipping and handling due to bruising. The firmness of the fruit flesh is sufficient to allow the flesh to yield and be restored when bumped or dropped without the resulting soft spots as would be experienced in most late season peaches of this market class. Thus, fruit of this tree remains more attractive to the ultimate buyer, the consumer, and thereby will command premium prices for the late fresh desert market.

The fruit matures in the latter part of the peach growing season of southwestern Michigan. The fruit as mentioned heretofore is of light red color overlying a yellow which covers approximately thirty percent (30%) of its surface and has a very attractive appearance.

BRIEF DESCRIPTION OF THE PHOTOGRAPHS

In the accompanying photographic illustrations, the top photograph, taken at harvest stage, shows 5 attached whole fruit in different orientations and the branching of stems of fruiting wood of this tree. The bark color of bearing wood, top and bottom leaf surfaces, leaf midribs, fruit skin color and substantially solid blush of fruit skin coloration are illustrated. The inserted pistil point of the fruit, the medium suture, and the exceptional shape and the characteristic symmetry of the fruit of this tree are depicted in this photograph.

The bottom photograph depicts, at the top, a typical fruit at ripeness bisected on the suture plane to show the flesh color, the color of the flesh at the surface of the pit well; and the stone with a tape measure on the right. Below the top fruit is a second fruit bisected across the axis of the fruit to show, on the left, the extent of the red coloration of flesh from the pit well as well as the intimate association of flesh the the stone, on the right hand side.

DESCRIPTION OF VARIETY

The detailed botanical description of the foliage and fruit of the new variety of peach tree is based upon observation of the specimens grown at Coloma, Mich. with the color terminology, other than the terminology expressed in common terms, in accordance with the Panatone Matching System (PMS) as used internationally to identify printed colors.

Tree:
- *Height.*—Medium to large unpruned 18'.
- *Width.*—Unpruned 14'.
- *Size.*—Large.
- *Vigor.*—Medium vigor terminal growth of about 24" per year.
- *Density.*—Medium.
- *Form.*—More upright than spreading; normally taller than wide. Scaffold branches are strong with little or no bark encroachment in crotches. Trees are easily maintained to have a narrow rounded upright to base-like figure, but are adaptable to other training systems by pruning if desired.
- *Production.*—Productive, requires some thinning annually.
- *Bearer.*—Consistent.
- *Disease resistance to bacterial leaf and fruit spot.*—Very good.

Trunk:
- *Size.*—Medium to stocky.
- *Surface.*—Medium shaggy.

Branches:
- *Size.*—Medium.
- *Surface.*—Smooth to medium.
- *Lenticels.*—Medium number and medium size.
- *Color.*—Grayish brown.

Leaves:
- *Size.*—Medium. Average length — 5" to 6". Average width — 1⅛".
- *Form.*—Lanceolate — pointed.
- *Thickness.*—Medium.
- *Texture.*—Medium.
- *Margin.*—Serrate.
- *Petiole.*—Medium length — medium thickness.
- *Gland.*—0 to 1 on each side of leaf and very small or partial when present.
- *Color.*—Upper surface: green (350c). Bottom: dull green (349c).

Flower buds:
- *Size.*—Medium.
- *Length.*—Medium.

Flowers:
- *Blooming period.*—May 1, 1995 to May 6, 1995, mid-season.
- *Size.*—Medium — about ¾" diameter.
- *Pollen.*—Present, self-fertilizing.
- *Color.*—Pink.

Fruit:
- *Maturity when described.*—Firm ripe.
- *Date of first picking.*—Sep. 8, 1995. Fruit can be harested in about four pickings.
- *Date of last picking.*—Sep. 16, 1995.
- *Size.*—Large sphere. Average diameter — 2⅝".
- *Form.*—Spherical.
- *Suture.*—Medium.

Skin:
- *Thickness.*—Medium.
- *Texture.*—Medium.
- *Tendency to crack.*—None.
- *Down.*—Moderate to little.
- *Color.*—Fruit is attractive, although the red color is somewhat light and dull (1805c) about 30% is ground color yellow (106u).

Flesh:
- *Texture.*—Firm — non-melting.
- *Ripens.*—Evenly.
- *Flavor.*—Excellent, more sweet than acidic.
- *Aroma.*—Pleasant.
- *Eating quality.*—Excellent.
- *Color.*—Clear Yellow (106u). Red around pit (1795u).

Stone:
- *Type.*—Freestone.
- *Size.*—Average length — 1¼". Average width — 1 1/16". Average thickness — ¾".
- *Form.*—Roundish ovid.
- *Base.*—Straight.
- *Apex.*—Rounded.
- *Sides.*—Nearly equal.
- *Surface.*—Irregularly furrowed.
- *Color.*—Mostly very dark brown (4975u) with tinges of dark red (201c).
- *Tendency to crack.*—None.
- *Harvest date.*—Determined when pit color appears.

Use: Desert.

Shipping quality: Excellent; permits widespread distribution over prolonged periods.

Keeping quality: Excellent; shelf life longer lasting.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described as large size, vigorous and upright in growth, a regular and productive beared of large size, yellow flesh freestone fruit with good flavor and shipping quality and having a late season maturity date of about Sep. 8, 1995.

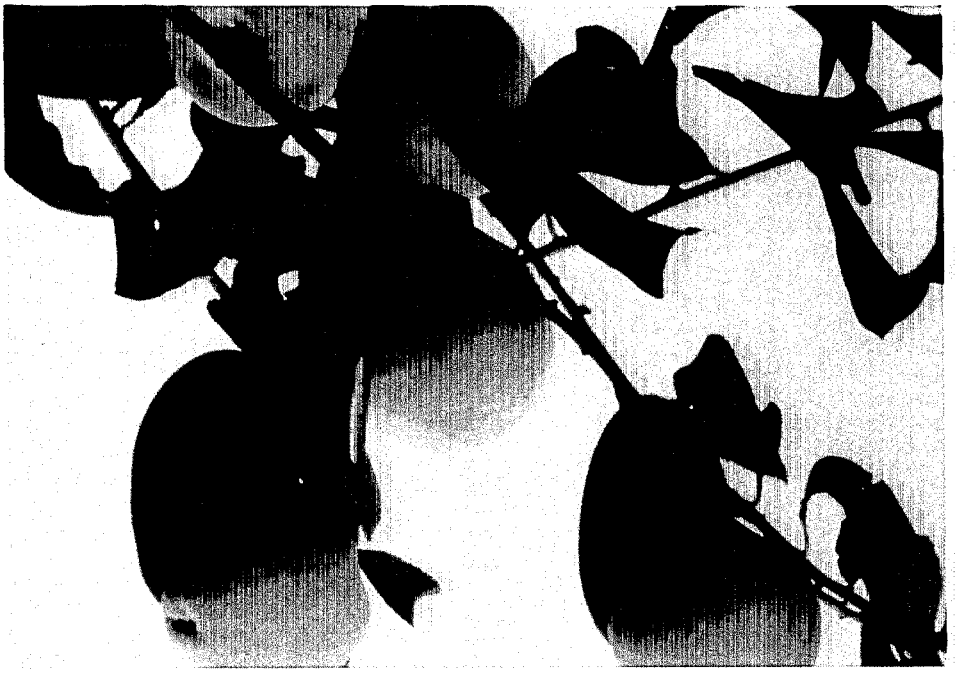
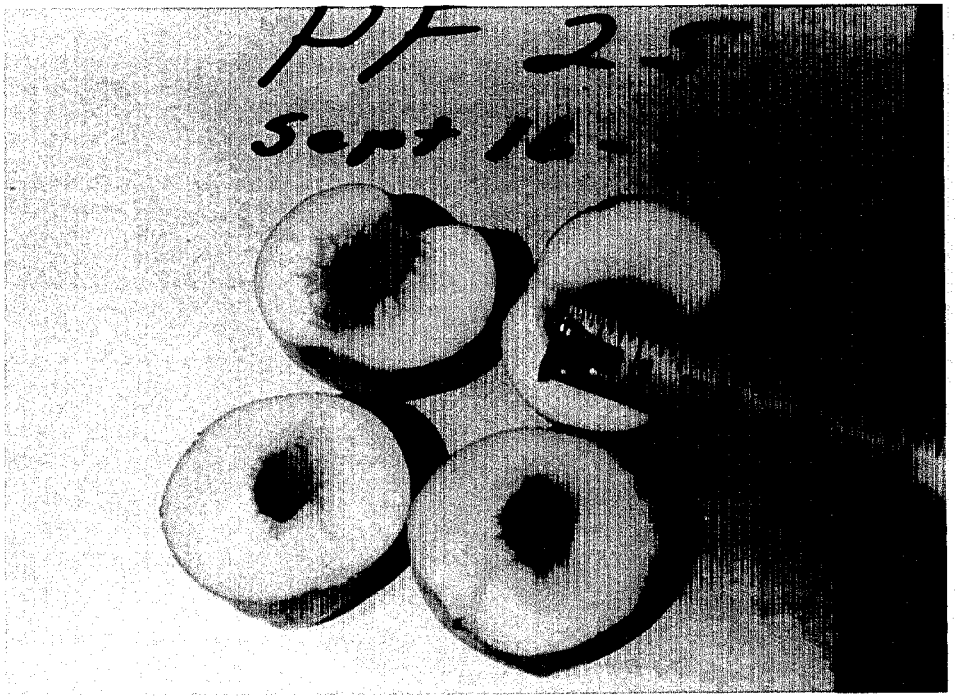

* * * * *